United States Patent [19]

Tomiyama et al.

[11] Patent Number: 4,730,060
[45] Date of Patent: Mar. 8, 1988

[54] CARBACYCLIN DERIVATIVES, METHOD OF MANUFACTURING THE SAME AND THERAPEUTIC AGENTS CONTAINING THESE COMPOUNDS

[75] Inventors: Tsuyoshi Tomiyama, Sakaki; Akira Tomiyama, Togura; Takashi Yanagisawa, Koushoku; Masayuki Yokota, Sakaki, all of Japan

[73] Assignee: Kotobuki Seiyaku Co. Ltd., Nagano, Japan

[21] Appl. No.: 57,359

[22] Filed: Jun. 1, 1987

[30] Foreign Application Priority Data

Jul. 8, 1986 [JP] Japan .................................. 61-161445
Dec. 9, 1986 [JP] Japan .................................. 61-291467

[51] Int. Cl.$^4$ ............................................. C07C 177/00
[52] U.S. Cl. .................................... 549/362; 549/434; 560/119; 560/56
[58] Field of Search ................. 549/362, 434; 560/119, 560/56; 514/530, 573

[56] References Cited

U.S. PATENT DOCUMENTS

| 4,436,934 | 3/1984 | Larock | 560/119 |
| 4,487,960 | 12/1984 | Lin | 560/56 |
| 4,533,749 | 8/1985 | Aristoff | 560/56 |
| 4,618,626 | 10/1986 | Skuballa | 560/119 |

FOREIGN PATENT DOCUMENTS

| 153822 | 9/1985 | European Pat. Off. |
| 3335389 | 4/1984 | Fed. Rep. of Germany |
| 61-30554 | 2/1986 | Japan |
| 83/3248 | 9/1983 | PCT Int'l Appl. |
| 2017699 | 10/1979 | United Kingdom |

OTHER PUBLICATIONS

Tobimatsu, M. et al, Fac. Med. Kyushu Univ. Ann Surg., 205(2) 199–202, 1987.

Adaikan, P. G. et al; Prostaglandins, Leukotrienes, Med 10(1), 53–64, 1983.

*Primary Examiner*—Paul J. Killos
*Attorney, Agent, or Firm*—Emmanuel J. Lobato; Robert E. Burns

[57] ABSTRACT

New agents of carbacyclin derivatives are disclosed, which are represented by the following formula:

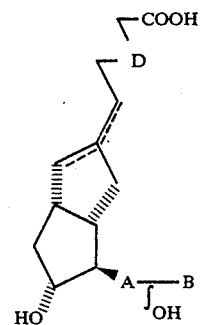

wherein A is a —CH=CH— or —C≡C— group. B is a substituted or unsubstituted indanyl group, substituted or unsubstituted benzodioxanyl group, substituted or unsubstituted benzodioxolanyl group or 2,3,5,6,7, 8-hexahydrobenzodioxanyl group. D is —CH$_2$— or —O—. ~OH group represents α or β configuration of OH group; and

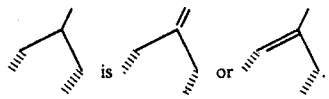

These compounds are useful as anit-ulcer, anti-hypertensive or anti-thrombotic agents.

14 Claims, No Drawings

CARBACYCLIN DERIVATIVES, METHOD OF MANUFACTURING THE SAME AND THERAPEUTIC AGENTS CONTAINING THESE COMPOUNDS

BACKGROUND OF THE INVENTION

This invention relates to new prostacyclin derivatives and their alkali addition salts, a method of their synthesis and use for medicals.

It is said that prostacyclin is unstable and has wide divergent and systemic biological activities.

Therefore, stable prostacyclin analogues having selective biological effects are desired for medical use.

Prostacyclin (PGI$_2$) is known to have an action of anti-thrombotics, vasodilatives or anti-ulceratives.

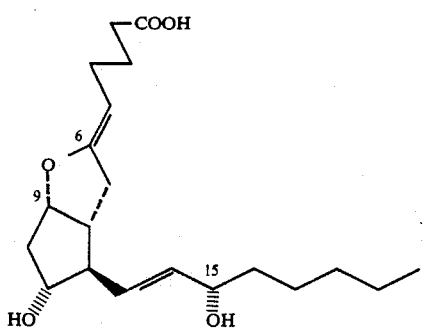

(PGI$_2$)

Oxygen atom between 6,9 positions is chemically unstable and therefore more stable prostacyclin analogues are investigated.

In the aforesaid formula of prostacyclin, prostacyclin analogues having oxygen atom at 6,9-position (—O—) replaced by carbon atom (—CH$_2$—), are synthesized (Stanley M. Roberts & Feodor Scheinmann Eds.; New Synthetic Routes of Prostaglandins and Thromboxanes, Academic Press (1982), 221-31p.).

Moreovre, it is known that prostaglandin analogues are dehydrogenated to 15-ketoprostaglandin by 15-hydroxyprostaglandin dehydrogenase to lose their activities. (Jarabak J. and Braithwaite S. S.; Arch. Biochem. Biophys. (1976), 177-245p.). By introducing a triple fond (—C≡C—) at 13 position, prostaglanedins can be stabilized from inactivation due to 15-hydroxyprostaglandin dehydrogenase. (Josef Fried, D. K. Mitra, M. Nagarajan & M. M. Mohrotra; J. Med. Chem. 23, 234–7p. (1980)).

DETAILED DESCRIPTION OF THE INVENTION

This invention, under these circumstance, relates to new and chemically stable and biologically selective prostaglandin derivatives and more particularly to carbacyclin or isocarbacyclin derivatives that are substituted by a bicyclo group in ω chain of carbacyclin and such compounds are confirmed to have several excellent proterties to meet the requirements mentioned above.

The compounds of this invention have the following general formula(I)

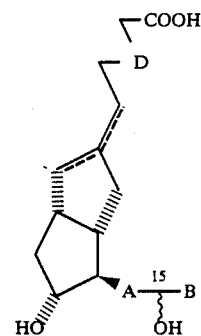

wherein: A is a —CH═CH— or —C≡C— group, B is a substituted or unsubstituted indanyl group, substituted or unsubstituted benzodioxanyl group, substituted or unsubstituted benzodioxolanyl group or 2,3,5,6,7,8-hexahydrobenzodioxanyl group, D is —CH$_2$— or —O—, ~OH group is α or β-configuration of OH group;

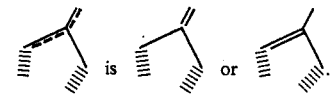

and pharmaceutically acceptable alkali addition salts thereof.

As substituent groups in bicyclo of said B, a lower alkyl group of C$_{1\sim5}$, a lower alkyloxy group of C$_{1\sim3}$, halogen or nitro group are cited.

A compound having a bicyclo compound in ω chain (lower chain) of prostaglandins or their analogues has not been reported so far, therefore, the compound of formula(I) is also a new compound.

In case carbon atom of β-position in α (upper)chain is substituted by oxygen atom, such compounds are not subject to β-oxidation.

The compound having a bicyclocompound in ω chain is expected not subject to ω-oxidation of ω-chain and oxidation of 15-hydroxy group with 15-hydroxyprostaglandin dehydrogenase and can be inhibited by steric hindrance of a bulky bicyclo compound.

For this reason, the compound of this invention is considered such that the conversion of the compound to 15-ketoprostaglandin may be slight so as to show a low level of inactivation. In case a bicyclo compound contains a hetero atom, the 15-hydroxy group is stabilized by forming a hydrogen-bond between 15-hydroxy group and a hetero atom and considered not susceptible to the inactivation with 15-hydroxyprostaglandin dehydrogenase.

Some compounds of this invention are obtained in crystal form. The compounds related to the general formula(I) are examplified as follows.

(1) 15α-Hydroxy-15-(benzodioxane-6-yl)-carbacyclin
(2) 15β-Hydroxy-15-(benzodioxane-6-yl)-carbacyclin
(3) 13,14-Dehydro-15α-hydroxy-15-(indan-2-yl)-carbacyclin
(4) 13,14-Dehydro-15β-hydroxy-15-(indan-2-yl)-carbacyclin
(5) 15α-Hydroxy-15-(benzodioxane-2-yl)-carbacyclin
(6) 15β-Hydroxy-15-(benzodioxane-2-yl)-carbacyclin
(7) 15α-Hydroxy-15-(indan-2-yl)-carbacyclin
(8) 15β-Hydroxy-15-indan-2-yl)-carbacyclin (9) 15α-Hydroxy-15-(6-methylbenzodioxane-2-yl)-carbacyclin
(10) 15β-Hydroxy-15-(6-methylbenzodioxane-2-yl)-carbacyclin
(11) 15α-Hydroxy-15-(6-methoxybenzodioxane-2-yl)-carbacyclin
(12) 15β-Hydroxy-15-(6-methoxybenzodioxane-2-yl)-carbacyclin
(13) 15α-Hydroxy-15-(2,3,5,6,7,8-hexahydro-benzodioxane-2-yl)-carbacyclin
(14) 15β-Hydroxy-15-(2,3,5,6,7,8-hexahydro-benzodioxane-2-yl)-carbacyclin
(15) 15α-Hydroxy-15-(benzodioxane-2-yl-methyl)-carbacyclin
(16) 15β-Hydroxy-15-(benzodioxane-2-yl-methyl)-carbacyclin
(17) 15β-Hydroxy-15-(2-methylbenzodioxane-2-yl)-carbacyclin
(18) 15β-Hydroxy-15-(2-methylbenzodioxane-2-yl)-carbacyclin
(19) 15α-Hydroxy-15-(indan-6-yl)-carbacyclin
(20) 15β-Hydroxy-15-(indan-6-yl)-carbacyclin
(21) 15α-Hydroxy-15-(indan-1-yl)-carbacyclin
(22) 15β-Hydroxy-15-(indan-1-yl)-carbacyclin
(23) 15α-Hydroxy-15-(5-nitroindan-2-yl)-carbacyclin
(24) 15β-Hydroxy-15-(5-nitroindan-2-yl)-carbacyclin
(25) 15α-Hydroxy-15-(5-methoxyindan-2-yl)-carbacyclin
(26) 15β-Hydroxy-15-(5-methoxyindan-2-yl)-carbacyclin
(27) 15α-Hydroxy-15-(5-chloroindan-2-yl)-carbacyclin
(28) 15β-Hydroxy-15-(5-chloroindan-2-yl)-carbacyclin
(29) 15α-Hydroxy-15-(benzoidoxolan-5-yl)-carbacyclin
(30) 15β-Hydroxy-15-(benzodioxolan-5-yl)-carbacyclin
(31) 15α-Hydroxy-15-(2-methylindan-2-yl)-carbacyclin
(32) 15β-Hydroxy-15-(2-methylindan-2-yl)-carbacyclin
(33) 15α-Hydroxy-15-(2-methylindan-2-yl)-3-oxa-carbacyclin
(34) 15β-Hydroxy-15(2-methylindan-2-yl)-3-oxa-carbacyclin
(35) 15α-Hydroxy-15-(indan-2-yl)-3-oxa-carbacyclin
(36) 15β-Hydroxy-15-(indan-2-yl)-3-oxa-carbacyclin
(37) 15α-Hydroxy-15-(1,4-benzodioxane-2-yl)-3-oxa-carbacyclin
(38) 15β-Hydroxy-15-(1,4-benzodioxane-2-yl)-3-oxa-carbacyclin
(39) 15α-Hydroxy-15-(6-methoxy-1,4-benzodioxane-2-yl)-3-oxa-carbacyclin
(40) 15β-Hydroxy-15-(6-methoxy-1,4-benzodioxane-2-yl)-3-oxa-carbacyclin
(41) 15α-Hydroxy-15-(2-methylindan-2-yl)-3-oxa-isocarbacyclin
(42) 15β-Hydroxy-15-(2-methylindan-2-yl)-3-oxa-isocarbacyclin
(43) 15α-Hydroxy-15-(indan-2-yl)-3-oxa-isocarbacyclin
(44) 15β-Hydroxy-15-(indan-2-yl)-3-oxa-isocarbacyclin
(45) 15α-Hydroxy-15-(1,4-benzodioxane-2-yl)-3-oxa-isocarbacyclin
(46) 15β-Hydroxy-15-(1,4-benzodioxane-2-yl)-3-oxa-isocarbacyclin The above-mentioned compounds numbered from (1), (2), - - - to (46) will be refered to hereinafter, as compound(1), compound(2), - - - compound(46) respectively. In manufacturing the compounds of this invention, the starting material related to the general formula(II)

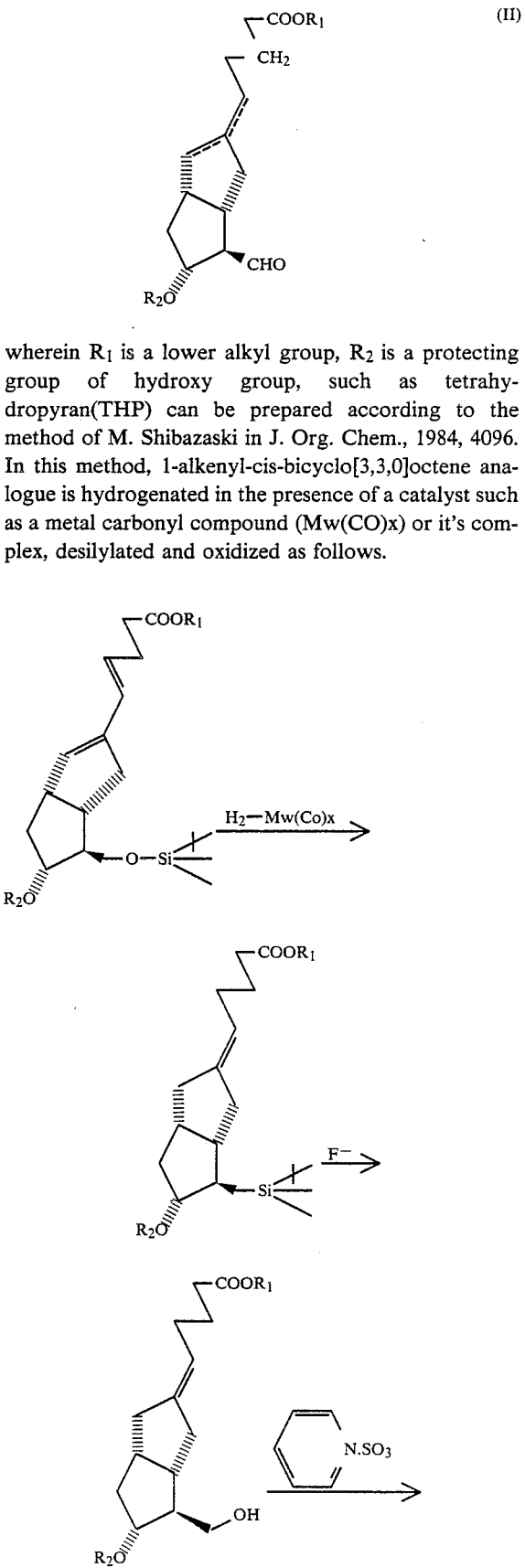

wherein $R_1$ is a lower alkyl group, $R_2$ is a protecting group of hydroxy group, such as tetrahydropyran(THP) can be prepared according to the method of M. Shibazaski in J. Org. Chem., 1984, 4096. In this method, 1-alkenyl-cis-bicyclo[3,3,0]octene analogue is hydrogenated in the presence of a catalyst such as a metal carbonyl compound (Mw(CO)x) or it's complex, desilylated and oxidized as follows.

-continued
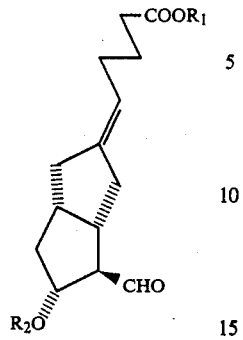
(II)
In manufacturing the compounds of this invention, the starting material related to the general formula(III).
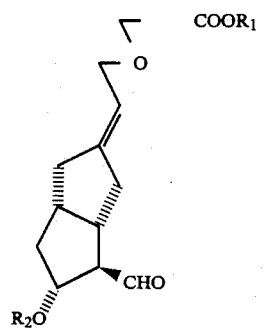
(III)
wherein $R_1$ is a lower alkyl group and $R_2$ is a protecting group of hydroxy group, can be prepared according to the method of Shibazaki and Yokota (Japan Pharmaceutical Association Annual meeting(1985). Abstract 610p.).
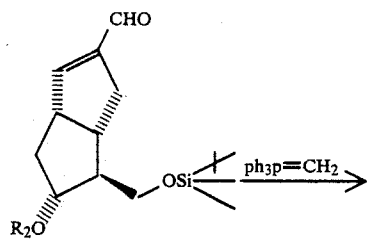
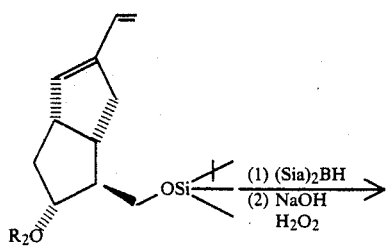
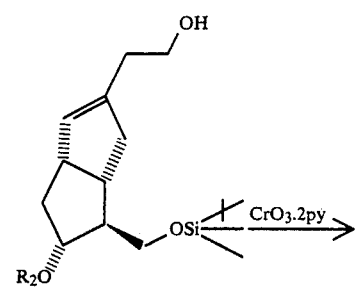
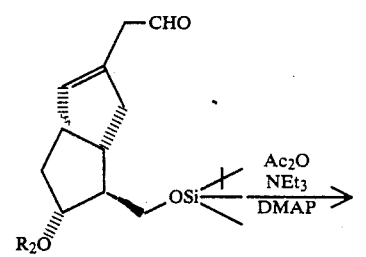
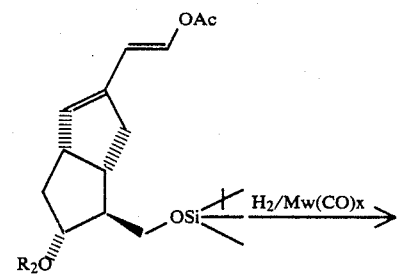
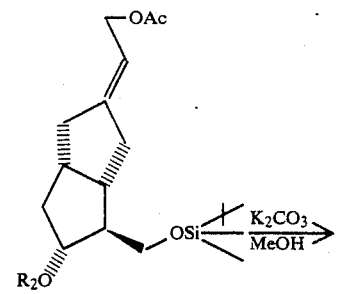
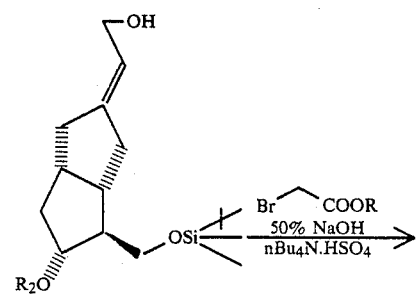

-continued

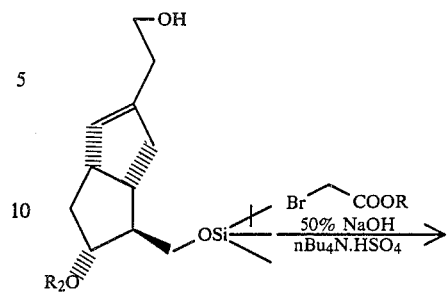

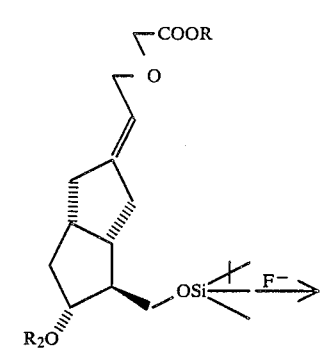

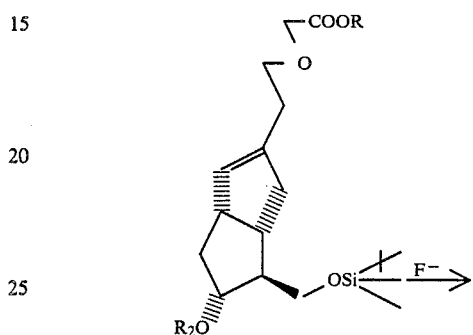

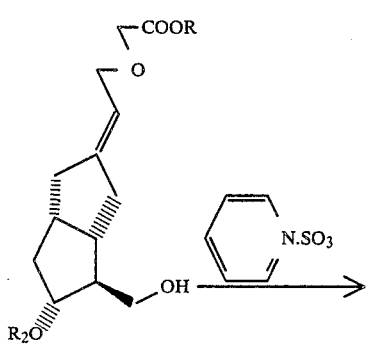

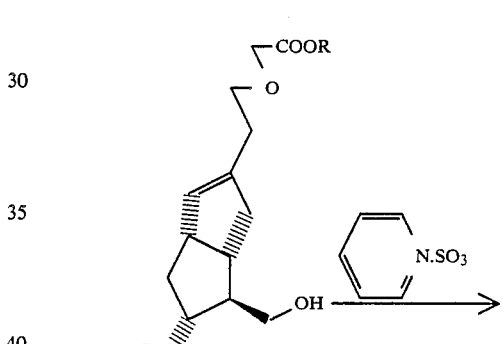

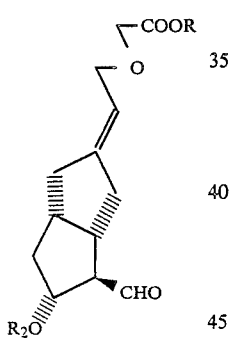

Starting material related to the general formula(IV)

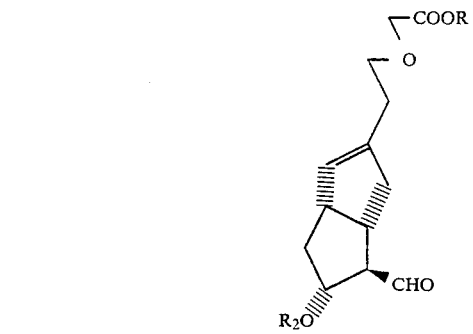

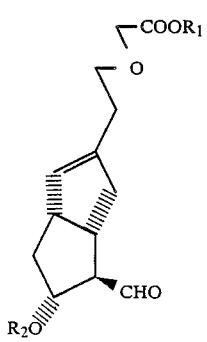 (IV)

wherein $R_1$ is a lower alkyl group and $R_2$ is a protecting group, is prepared as follows.

The compounds of this invention are obtained as follows. The reaction of compounds of general formulas(II~IV) with the compound of general formula(V):

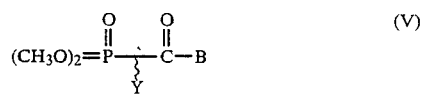 (V)

wherein B is as defined above, Y is hydrogen or halogen atom, to obtain the compound of general formula(VI):

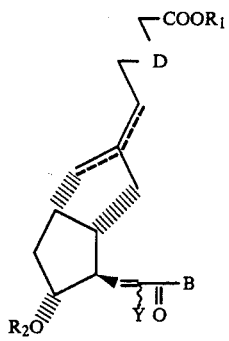

wherein $R_1$, $R_2$, Y, B and D are defined above. This reaction can be generally carried out by Wittig reaction. As the solvent used in this reaction, the following ones are mentioned such as ethers (ethylether, tetrahydrofuran, dimethoxyethan), hydrocarbons (hexan, benzene), amides (dimethylformamide, dimethylacetamide), dimethylsulfoxide or hexamethylphosphamide. As the base used in this reaction, the following bases are mentioned such as organolithium compounds (n-butyl lithium, phenyl lithium, lithium diisopropylamide) alkalimetal alkoxide (aodium ethoxide, potassium t-butoxide) or NaH-DMSO (dimusyl anion). 15-Oxo compound shown in formula(IV) is obtained as a mixture of cis(Z) and trans(E) isomer and if necessary, cis(Z) and trans(E) isomer are isolated by means of chromatography.

The compound shown in formula(VI) is reduced to a 15-hydroxy compound of formula(VII).

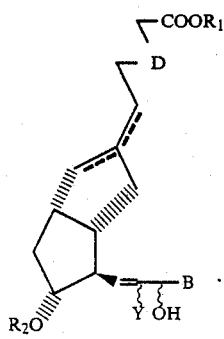

wherein $R_1$, $R_2$, Y, OH, B and D are same as mentioned above. In this reduction, sodium borohydride, lithium aluminium hydride or selectide are used.

The 15-Hydroxy compound shown in formula(VII) is a mixture of α-hydroxy and β-hydroxy isomer and this mixture is occasionally separated to α-isomer and β-isomer using chromatographical technics.

Moreover, in case Y is halogen atom in the compound of formula(VII), the compound of formula(VII) is subjected to dehydrohalide reaction and deprotection reaction. Then the compound shown in formula(I) in which A is a triple bond (—C≡C—) is obtained. The base used in this dehydrohalide reaction is mentioned such as potassium t-butoxide or potassium acetate. In case potassium t-butoxide is used, dehydrohalide and hydrolysis of ester proceed simultaneously.

The compound shown in formula(VII) in which Y is hydrogen, is subjected to deprotection of hydroxy group, giving a obtained 11-hydroxy compound. This 11-hydroxy compound is occasionally separated to a 15-αhydroxy compound and 15β-hydroxy compound by means of chromatography.

Deprotection of the 11-hydroxy group is carried out in a diluted acetic acid solution. In this case, after deprotection of the 11-hydroxy group of formula(VII), the resulting compound is subjected to hydrolysis of the ester group (—COOR$_1$) with a base leading to the compound of formula(I).

In case Y is halogen atom in the compound of general formula(V), the compound can be obtained by reacting the compound of general formula(V) in which Y is hydrogen with a halogenation regaent such as N-chlorosuccine imide (N.C.S.), N-bromosuccine imide (N.B.S.) etc.

For example,

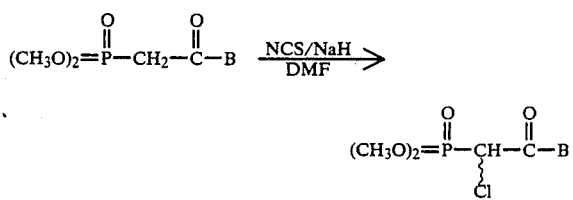

B in general formula(I) represents indanyl, benzodioxanyl, benzodioxolanyl or 2,3,5,6,7,8-hexahydrobenzo dioxanyl group and these substituted bicyclo compounds.

Substituent in the bicyclo ring, in this case, means a lower alkyl, a lower alkoxyloxy, nitro group or halogen atom and these bicyclo compounds are described in literature.

Among these bicyclo compound, uncommon compounds are prepared as follows.

(1) In case B is 2-methylindanyl group, a product can be obtained as follws.

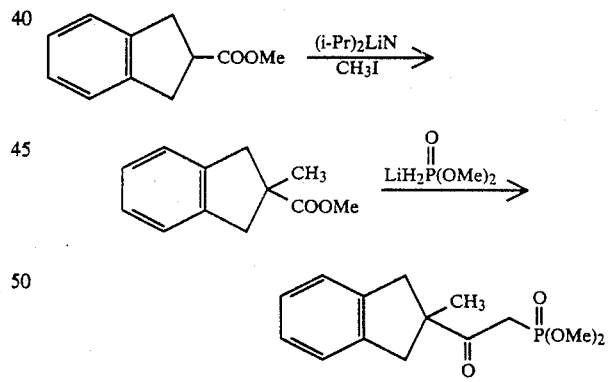

(2) In case B is 2-methylbenzodioxanyl group, a product can be obtained as follows.

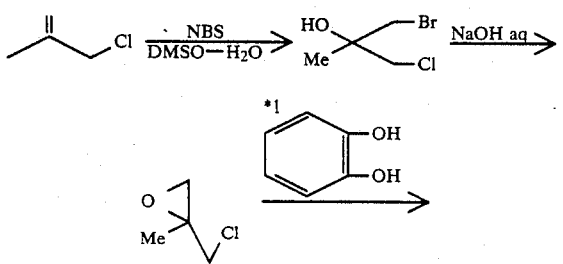

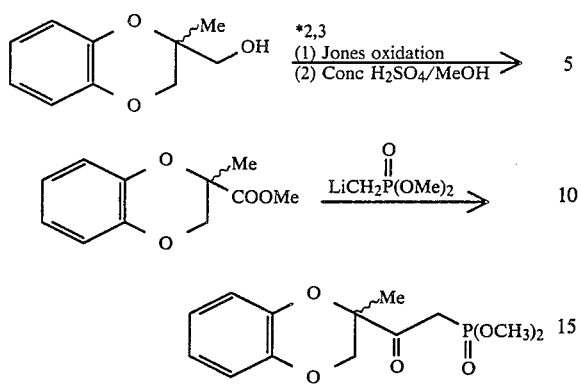

(3) In case a compound of the formula I in which B is 2,3,5,6,7,8-hexahydrobenzodioxanyl group, a product can be obtained according to the method cited in Chem. Abst. 57, 16633c and Ibid. 61, 13320a as follows.

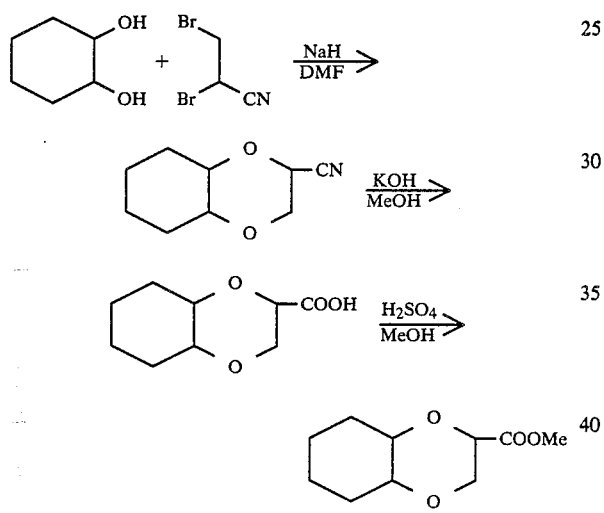

The compounds shown in the formula(I) and pharmaceutically acceptable alkali addition salts thereof in formula(I) have an excellent anti-ulcerative, anti-thrombotic and vasodilating action which will be explained later. Also the compounds of this invention are chemically stable and are administered orally or parenterally. An effective dosage depending on age and symptoms, is from 100 µg to 1000 µg a day for adults.

Pharmaceutical and experimental examples of the compounds of this invention are as follows.

[PHARMACOLOGICAL EXAMPLE]

1. Anti-ulcer activities, Ethanol-induced ulcer

Inhibitory effects of ethanol-induced ulcer are determined by the method of A. Robert (Gastroenterology 77, 433-43). Rats are fasted for 24 hrs. and are given 1 ml of absolute ethanol perorally. 1 hour after administration of ethanol, the stomach of the rat is removed. The length of each ulcer occurring in the grandulor stomach is determined and each ulcer in one rat is acounted as ulcer-index. The test compounds are given perorally 30 minutes before ethanol administration. The results are shown Table 1.

TABLE 1

| Test Compound | Dose (µg/kg) | Inhibition (%) |
| --- | --- | --- |
| Compound 1 | 100 | 41.6 |
| Compound 3 | 30 | 93.4 |
| Compound 5 | 10 | 71.9 |
| Compound 7 | 100 | 68.7 |
| Compound 9 | 300 | 80.6 |
| Compound 11 | 30 | 82.1 |
| Compound 17 | 100 | 72.6 |
| Compound 23 | 300 | 98.9 |
| Compound 33 | 30 | 47.6 |
| Compound 35 | 30 | 44.6 |
| Compound 37 | 100 | 51.6 |
| Compound 41 | 10 | 64.2 |
| Compound 43 | 100 | 51.8 |
| Compound 45 | 10 | 58.9 |

2. Anti-hypertensive activities

The anti-hypertensive activities of the compounds on anesthetized normotensive rats were tested according to the method of H. Sogabe*. Male Wistar rats weighing 200~300 g were anesthetized with urethane (1.2 g/kg i.p.). A polyethylene catheter was inserted into the femoral artery and blood pressure was measured by a transducer (Nihon Kohden, TP-200T) connected to the catheter. Heart rate was monitored by the cardiotachometers (Nihon Kohden, RT-5) and recorded simultaneously. The test compounds in physiological saline (0.1 ml/100 g B.W.). were injected via the femoral vein. The anti-hypertensive activity was assessed by comparing with M B $P_{15}$ (dose which lowers the mean blood pressure by 15 mmHg, mg/kg i.v.). The results are shown in Table 2.

*Hirobumi Sogabe (Jikken Kouketsuatsushou nyumon, 227p.; Eikoudo 1968)

TABLE 2

| Compound No. | Anti-hypertensive act. ($MBP_{15}$) |
| --- | --- |
| 3 | 1.35 (µg) |
| 5 | 2.0 |
| 7 | 4.2 |
| 9 | 80.6 |
| 11 | 34.7 |
| 13 | 13.5 |
| 17 | 9.3 |
| 23 | 8.5 |
| 25 | 32.4 |
| 33 | 7.6 |
| 35 | 2.2 |
| 37 | 2.5 |
| 41 | 2.0 |
| 45 | 1.7 |

3. Anti-thrombotic activities

Blood was taken from the abdominal aorta of rat into a plastic syringe containing a trisodium citrate solution (3.8%; 0.1 volume with 0.9 volume blood) under ether anesthesia. Platelet aggregation was measured with an aggregometer (Chrono-Log corp., U.S.A. Type C530) according to the method of David C. Cardinal et al.*. Blood (985 µl) was taken into a cuvette and maintained at 37° C. Test compound was added into it 2 min prior to addition of collagen reagent (5 µl), 5 µg/ml at final concentration) and an aggregative curve was recorded. Platelet aggregation was expressed by a value of electrical impedence. The maximum aggregation of control was indicated as 100% and that of treated with the drug was expressed by inhibitory percent.

*D.C. Cardinal et al.; J. Pharmacol. Methods 3, 135-58, 1980

TABLE 3

| Compound No. | IC$_{50}$ (ng/kg) |
| --- | --- |
| 3 | 8.2 |
| 5 | 323.6 |
| 7 | 20.4 |
| 11 | 355.0 |
| 23 | 150.8 |
| 25 | 70.5 |
| 27 | 407.3 |
| 31 | 30.2 |
| 35 | 46.7 |
| 41 | 69.2 |
| 43 | 15.3 |
| 45 | 53.1 |

4. Stability test

About 1.5 mg of test compound was dissolved in a drop of methanol and diluted in each 1.5 ml of a buffer solution *adjusted to pH 5.2, 7.2, 7.4, 9.2, respectively. Stability test was carried out at 37° C. in the case of pH 5.2, 7.2, 9.2 and at room temperature in the case of pH 7.4,.

Using a thin layer chromatography as the identification method, the test solution in each buffer solution of pH 5.2, 7.2, 7.4 was extracted with ethyl acetate and in the case of the test solution of pH 9.4, it was diluted with water, acidified at pH 4 with 10% HCl and extracted with ethyl acetate. The change of each extract in thin layer chromatography is shown in Table 4.

*pH 5.2 (0.2M Pottasium hydrogen phthalate)
pH 7.2 (0.2M KH$_2$PO$_4$+0.2N-NaOH)
pH 7.4 (0.2M KH$_2$PO$_4$+0.2N-NaOH)
pH 9.2 (0.2M KH$_2$PO$_4$+0.2M KCl+0.2N-NaOH)

TABLE 4

| Compound 5 | pH 7.4 | 2 months | No change |
| --- | --- | --- | --- |
| Compound 7 | pH 5.2 | 120 min | " |
| Compound 5 | pH 7.2 | " | " |
| Compound 5 | pH 9.2 | " | " |

The compounds of general formula(I) can be applied mainly in the form of granules, tablets or capsules as they are or in the form of their pharmaceutically acceptable alkali addition salts.

Pharmaceutical examples are as follows.

[PHARMACEUTICAL EXAMPLE 1]

Tablets of following ingredients.

| Compound 5 | 0.10 mg |
| --- | --- |
| Crystalline cellulose | 10.0 g |
| Lactose | 70.0 g |
| Corn starch | 35.0 g |
| Methyl cellulose | 3.0 g |
| Magnesium stearate | 2.0 g |
| Total | 120.0 g |

Above mentioned mixture is tableted in conventional manner to produce tablets, each containing 100 μg of compound 5.

[PHARMACEUTICAL EXAMPLE 2]

Capsules of following ingredients.

| Compound 7 | 0.20 mg |
| --- | --- |
| Crystalline cellulose | 10.0 g |
| Polyethylene glycol 6000 | 2.0 g |
| Lactose | 65.0 g |
| Corn starch | 23.0 g |
| Total | 100.0 g |

Above mentioned mixture is mixed in usual manner to produce a capsules, each containing 200 μg of compound 7.

[EXAMPLE 1~2]

15α-Hydroxy-15-(benzodioxan-6-yl)-carbacyclin
(Compound 1)

15β-Hydroxy-15-(benzodioxan-6-yl)-carbacyclin
(Compound 2)

(a)

(2-(Benzodioxan-6-yl)-2-oxo-9-ethyl-dimethyl phosphonate

A mixture of 18.0 g of methyl 3,4-dihydroxy benzoate, 5.2 ml of dibromoethane and 7.5 g of potassium carbonate in 60 ml of acetone was refluxed for 10 hours. After cooling, the reaction mixture was filtered rat and filtrate was evaporated. The residue was dissolved in ether, washed with water, 5% sodium hydroxide and brine. Hexan was added to the solution and allowed to stand still overnight. Resulting precipitate was collected by filtration and 15.2 g (73.3%) of the desired compound was obtained.

(b)

11α-Tetrahydropyranyl-15-oxo-15-(benzodioxan-6-yl)-carbacyclin methyl ester.

After 0.068 g of NaH was washed with n-pentane under N$_2$ atmosphere in 50 ml flask, NaH was suspended in 1.3 ml of THF. To this solution, the solution of 0.873 g (2-benzodioxan-6-yl)-2-oxo)-ethyl dimethyl phosphonate in THF (6 ml) was added and stirred for 20 minutes at 0 under N$_2$ atmosphere and a solution of 0.45 g of aldehyde of formula II (R$_2$=THF) in THF(8 ml) was added. After stirring it for 30 minutes at room temperature, a saturated NH$_4$Cl solution was added to the mixture The mixture was extracted with ether and the ether extract was washed with brine, dried (Na$_2$SO$_4$) and the solvent was removed. The residue was purified with silica gel chromatography (ether: n-hexan (1:4)) and 0.350 g (0.54%) of the desired oily compound was obtained.

I.R.(cm$^{-1}$) 2940, 2870, 1740, 1670, 1620, 1580, 1500, 1438.

N.M.R. (δ, CDCl$_3$) 7.45~7.75 (m. 3H), 6.8(dd+m), 5.2(t, 1H), 4.55(bs. 1H), 4.22(s, 4H), 3.6(s, 3H), 3.4(m. 1H).

(c)

11α-Tetrahydropyranyl-15α,β-hydroxy-15-(benzodioxan-6-yl)-carbacyclin methyl ester.

To a solution of 0.100 g of compound obtained in (b) in 1 ml of ethanol, 0.002 g of NaBH was added at −25° C. (dry ice/CHCl$_3$) under N$_2$ atmosphere and stirred for 15 minutes. After adding acetone at −25° C., and stirring for 20 minutes at room temperature, the mixture was neutralized (pH 7.0) with a satd. NH$_4$Cl solution. Methanol was removed in vacuo, and then the residue was extracted with ether and washed (NaCl satd. water), dried (Na$_2$SO$_4$) and the solvent was removed. The residue was chromatographed on silica gel, eluting with ether:n-hexan (2:1). 0.100 g (99.2%) of the desired compownd was obtained. I.R. (cm$^{-1}$, neat) 3450, 2950, 2880, 1740, 1600, 1510. N.M.R. (δ, CDC$_3$), 6.9(s, 3H), 5.75(bs. 2H), 5.1~5.6(m, 2H), 4.8(bs. 1H), 4.31(s, 4H), 3.8(s, 3H), 3.4~3.7(m, 1).

(d)

15α-Hydroxy-15-(benzodioxan-6-yl)-carbacyclin methylester and

15β-Hydroxy-15-(benzodioxan-6yl)-carbacyclin methylester.

A solution of 0.350 g. of compound obtained in (c) in 5 ml. of a mixture (HOAc:H$_2$O: THF=3:1:1) was stirred for 5 hours at 45°~50° C. The solvent was removed in vacuo and toluene was added to the residue and the solvent was removed in vacuo. The residue was chromatographed on silca gel, eluting with ether:n-hexan (4:1).

15α-Hydroxy-15-(benzodioxan-6-yl)-carbacyclin methyl ester 0.070 g (33.7%) was obtained from the more polar fraction.

I.R. (cm$^{-1}$, neat) 3350, 2940, 2870, 1730, 1580, 1500, 1440, 1380, 1280, 1240.

M.S. (m/e) 428(M+), 149(b.p.).

15β-Hydroxy-15-(benzodioxan-6-yl)-carbacyclin methyl ester 0.06 g (28.9%) obtained from the less polar fraction.

I.R. (cm$^{-1}$, neat) 3404, 2940, 2860, 1734, 1582, 1506, 1438, 1401, 1308, 1287.

M.S. (m/e) 441(M+-H$_2$O), 188(b.p.).

(e)

15α-Hydroxy-15-(benzodioxan-6yl-carbacyclin and

15β-Hydroxy-15-(benzodioxan-6yl)-carbacyclin.

0.040 g of 15α-Hydroxy-15-(benzodioxan-6-yl)-carbacyclin methyl ester obtained in (d) was dissolved in 0.4 ml of methanol, 0.4 ml of 10% NaOH sol. was added at 0° C., and stirred for 2 hrs. at 0° C. and 10 hrs. at room temperature. The reactant was adjusted to pH 7.0 with 10% HCl sol. and solvent was removed. NaCl-satd. water was added to the resulting aqueous solution, pH. was adjusted to 3~4 with 10% HCl soln. and extracted with ethyl acetate. Ethyl acetate extract was dried (Na$_2$SO$_4$) and evaporated in vacuo. 0.010 g (25.9%) of oily 15α-Hydroxy-15-(benzodioxan-6-yl)-carbacyclin was obtained. M.S. (m/e) 396(M$^{30}$ -H$_2$O), 149(b.p.).

In the same manner as mentioned above, 0.048 g of 15β-Hydroxy-15-(benzodioxan-6-yl)-carbacyclin was hydrolized and 15β-Hydroxy-15-(benzodioxan-6-yl)carbacyclin was obtained, 0.020 g (41%). M.S. (m/e) 396(M+-H$_2$O), 149(b.p.)

[EXAMPLE 3~4]

13,14-Dehydro-15α-hydroxy-15-(indan-2-yl)-carbacyclin (Compound 3) and 13,14-Dehydro-15β-hydroxy-15-(indan-2-yl)-carbacyclin (Compound 4)

(a) To a solution of 2.74 ml of dimethylphosphonate in 20 ml of THF, 15.8 ml of n-Butyllithium (1.6M in hexan) was added at −78° C., stirred for 30 min, and thereto was added a solution of 3.76 g of methyl-2-indan-carboxylate in THF (26.3 ml) at −78° C. After stirring for 2 hrs., satd. NH$_4$Cl soln. was added to the mixture and left at room temperature. The mixture was extracted with ethyl acetate and ethyl acetate extract was washed (NaCl-satd. water), dried (Na$_2$SO$_4$) and evaporated. The residue was chromatographed on silica gel, eluting with ethyl acetate. 3.89 g of the objective colourless oily objective compound was obtained. N.M.R. (δ, CDCl$_3$) 7.15(s, 4H), 3.85(s, 3H), 3.72(s, 3H), 3.08(2s, 2H), 3.33~3.08(dtm, 5H) I.R. (cm$^{-1}$, neat) 2944, 2848, 1707, 1458, 1257, 1182, 1029, 807, 756. M.S. (m/e) 268(M+), 116(b.p.)

(b) (2-(Indan-2-yl)-2-oxo-1-chloro)-ethyl-dimethylphosphonate

In a 25 ml of two necked flask, 0.094 g of NaH was suspended in 1.6 ml of dimethoxyethan (DME) at 0° C. and 0.630 g of (2-(Indan-2-yl)-oxo-1-chloro)-ethyl dimethyl phosphonate in DME (11.0 ml) was added. The mixture was stirred for 30 minutes and 0.315 g of N-Chloro succinimide was added. After stirring 1 hour, to the mixture was added NH$_4$Cl satd. water and extracted with ether. Ether extract was washed with watwe, NaCl satd. water, dried (Na$_2$SO$_4$) and the solvent was removed in vacuo. The residue was chromatographied on silica gel, eluting with ethyl acetate:n-hexan (1:1). 0.351 g (49.0%) of the desired yellow compound was obtained. m.p. 57.3°~58.4° C. N.M.R. (δ, CDCl$_3$) 7.11(s, 4H), 4.93, 4.63(d, 1H), 3.91(s, 1H), 3.73(s, 3H) 3.34~3.65(m. 1H), 3.27, 3.14(d, 4H), I.R. (cm$^{-1}$, neat) 2944, 1728, 1460, 1378, 1266, 1180, 1035, 840, 750, M.S. (m/e) 303(M+), 115(b.p.)

(c) 14-Chloro-15-oxo-15-(indan-2-yl)-carbacyclin methyl ester

To a 25 ml of two necked flask, 0.1 ml of DME and 0.008 g of NaH was added at 0° C., 20 minutes at room temperature. After cooled to 0° C., a solution of 0.051 g of aldehyd in formula II (R$_2$=THF) in DME (1.2 ml) was added to the resulting mixture and stirred for 1 hour at 0° C., 2 hrs. at room temperature and 4 hrs. at 50° C. Adding with NH$_4$Cl satd. water at room temperature, the resulting mixture was extracted with ether. Ether extract was washed (brine), dried (Na$_2$SO$_4$) and evaporated in vacuo. The residue was chromatographied on silica gel (ether:n-hexan (1:4)). 6.022 g of objective compound (trans-isomer) was obtained from the less polar fraction. N.M.R. (δ, CDCl$_3$) 7.20(s, 4H), 6.22, 6.06(d, 1H), 5.21(bt, 1H) 4.68(bs, 1H), 3.65(s, 3H), 3.35, 3.20(d, 4H), 4.35~3.05(m, 4H), 2.77~1.15(m, 21H), I.R. (cm$^{-1}$, neat) 2932, 2854, 1734, 1695, 1440, 1350, 1320, 1248, 1197, 1167, 1119, 1074, 1010, 972, 867, 750.

(d) 11α-Tetrahydropyranyl-14-chloro-15α,β-hydroxy-15-(indan-2-yl)carbacyclin methyl ester In a 25 ml flask, 0.22 g of a compound obtained in (c) and methanol (2.2 ml) was added. 0.05 g of NaBH was added to the mixture at 0° C. and stirred for 15 minutes. After adding a small amount of acetone, the mixture was stirred for 30 minutes. Adjusting pH to 7.0 with satd. NH$_4$Cl soln, the mixture was evaporated in vacuo. After adding with satd. NaCl soln thereto, the residue was extracted with ether. Ether extract was washed (satd. NaCl soln), dried (Na$_2$SO$_4$) and the solvent was evaporated. Purification of the residue was carried out by silica gel chromatography (ether:n-hexan (2:1)). 0.180 g (81.5%) of the desired oily compound was obtained. N.M.R. (δ, CDCl$_3$) 7.10(s, 4H), 5.75, 5.61(d, 1H), 5.25(bt, 1H), 4.63(bs, 1H), 3.63(s, 3H), 4.21~3.20(m, 5H). I.R. (cm$^{-1}$, neat) 3418, 3004, 2932, 1731, 1437, 1356, 1317, 1218, 1200, 1170, 1119, 1074, 1020, 975.

(e) 14-Chloro-15α-hydroxy-15-(indan-2-yl)-carbacyclin methyl ester and 14-Chloro-15β-hydroxy-15-(indan-2-yl)-carbacyclin methyl ester 0.240 g of compound obtained in (d) was dissolved in 5 ml of a mixture of HOAc:H$_2$O:THF (3:1:1) and stirred for 8 hrs. at 45° C. and the solvent was evaporated. By distillation with toluene azeotropically, the residue was chromatographied on silica gel (ethyl acetate:n-hexan (1:1)). 0.071 g (34.8%) of oily 14-Chloro-15-α-hydroxy-15-(indan-2-yl)-carbacyclin methyl ester was obtained from the less polar fraction. N.M.R. (δ, CDCl$_3$) 7.17(s, 4H), 5.78, 5.61(d, 1H), 5.24(bt, 1H), 3.63(s, 3H), 4.29~3.44(mtd, 2H), 2.72~3.14(dtm, 5H), 2.71~1.01(m, 17H). I.R. (cm$^{-1}$, neat) 3394, 3004, 2932, 2842, 1725, 1437, 1218, 1080, 900, 750. In the same manner as mentioned above, 0.104 g (51.7%) of oily 14-Chloro-15β-hydroxy-15-(indan-2-yl)-carbacyclin methyl ester was obtained from the more polar fraction. N.M.R. (δ, CDCl$_3$) 7.10(s, 4H), 5.69, 5.51(d, 1H), 5.29(bt, 1H), 3.65(s, 3H), 3.39~4.30(m+d, 2H), 2.61~3.38(m+d, 5H), 1.0~2.61(m, 17H). I.R. (cm$^{-1}$, neat) 3370, 3004, 2932, 2836, 1725, 1437, 1215, 1083, 900, 753.

(f) 13,14-Dehydro-15α-hydroxy-15-(indan-2-yl)-carbacyclin and 13,14-Dehydro-15β-hydroxy-15-(indan-2-yl)-carbacyclin 0.030 g of 14-Chloro-15α-hydroxy-15-(indan-2-yl)-carbacyclin and dissolved in a mixture of DMSO (2 ml) and THF (1 ml) and thereto was added 0.038 g of potassium t-butoxide. After stirring for 10 hrs. at room temperature, the mixture was adjusted to pH 4.0 with 10% HCl soln. at 0° C. and extracted with ethyl acetate. Extract was washed (NaCl satd. water), dried (Na$_2$SO$_4$) and the solvent was evaporated. The residue was purified by thin layer chromatography. 0.021 g (79.0%) of objective 13,14-Dehydro-15α-hydroxy-15-(indan-2-yl)-carbacyclin was obtained. N.M.R. (δ, CDCl$_3$ 7.01(s, 4H), 4.93~5.40(bs+bt, 4H), 4.20~4.41(d, 1H), 3.50~4.10(m, 1H), 2.90(bs, 5H), 1.30~2.70(m, 15H). I.R. (cm$^{-1}$, neat) 3376, 2932, 2668, 2524, 1710, 1434, 1377, 1248, 1116, 1086, 1041, 975.

In the same manner as mentiond above, 0.013 g (48.9%) of 13,14-Dehydro-15β-hydroxy-15-(indan-2-yl)-carbacyclin was prepared from 0.030 g of 14-Chloro-15β-hydroxy-15-(indan-2-yl)-carbacyclin methyl ester. N.M.R. (δ, CDCl$_3$) 7.15(s, 4H), 5.22(bt, 1H), 4.55~5.06(bs, 3H), 4.30~4.52(d, 1H), 3.60 4.02(m, 1H), 2.99(bs, 5H), 1.37~2.70(m, 15H). I.R. (cm$^{-1}$, neat) 3370, 2930, 1728, 1434, 1377, 1245, 1083, 1041.

The following compounds were obtained in the same manner as the methods of Examples 1~2.

| Comp. | 15-Position | Z | B | appearance | Physical properties |
|---|---|---|---|---|---|
| 5 | α | COOH | benzodioxole-CH$_2$CH$_2$- | oil | MS(m/e) 414(M$^+$) NMR(δ) CDCl$_3$ 6.80(s,4H), 5.61(b.s+m,5H), 5.2(b.t,1H), 3.30~4.40(m,5H) IR cm$^{-1}$ (neat) 3406, 2926, 1713 |
| 6 | β | COOH | benzodioxole-CH$_2$CH$_2$- | oil | MS(m/e) 414(M$^+$) NMR(δ) CDCl$_3$ 6.85(s,4H), 5.75(m,2H), 5.40(s+b.t,4H), 3.40~4.60(m,5H) IR cm$^{-1}$ (neat) 3406, 2926, 1710 |
| 7 | α | COOH | indan-2-yl | White crystal mp 63.2~64.1° C. | MS(m/e) 378(M$^+$ −H$_2$O) NMR(δ) CDCl$_3$ 71.7(s,4H), 6.1(b.s,3H), 5.62(m,2H), 5.20(b.t,1H), 3.90~4.27(m,1H), 3.45~3.88(m,1H), 2.75~3.30(m,5H) IR cm$^{-1}$ (neat) 3360, 2926, 1710 |
| 8 | β | COOH | indan-2-yl | oil | MS(m/e) 378(M$^+$ −H$_2$O) NMR(δ) CDCl$_3$ 7.10(s,4H), 6.10(b.s,3H), 5.50(m,2H), 5.20(b.t,1H), 3.82~4.30(m,1H), 3.40~3.80(m,1H), 2.60~3.27(m,5H) IR cm$^{-1}$ (neat) 2926, 1725 |
| 9 | α | COOH | methyl-benzodioxole-CH$_2$CH$_2$- | oil | MS(m/e) 426(M$^+$ −2) NMR(δ) CDCl$_3$ 7.28(b.s,3H), 6.22, 6.20(s+d,3H), 5.67(m,2H), 5.27(b.t,1H), 3.50~4.44(m,5H), 2.29(s,3H) IR cm$^{-1}$ (neat) 3370, 2920, 1707 |

-continued

| Comp. | 15-Position | Z | B | appearance | Physical properties |
|---|---|---|---|---|---|
| 10 | β | COOH | 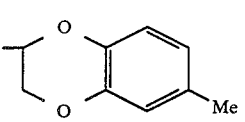 | oil | MS(m/e) 427(M$^+$ −1)<br>NMR(δ) CDCl$_3$<br>6.20, 6.18(s+d,3H), 5.70(m,2H),<br>5.20(b.t,4H), 3.50∼4.50(m,5H),<br>2.28(s,3H)<br>IR cm$^{-1}$ (neat) 3400, 2920, 1707 |
| 11 | α | COOH | 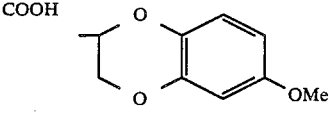 | oil | MS(m/e) 443(M$^+$)<br>NMR(δ) CDCl$_3$<br>6.40∼7.00(m,3H), 5.70(m,2H),<br>5.00∼5.50(b.s+b.c,4H),<br>3.72(s,3H), 3.90∼4.50(m,5H)<br>IR cm$^{-1}$ (neat) 3352, 2920, 1707 |
| 12 | β | COOH | 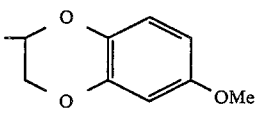 | oil | MS(m/e) 444(M$^+$ +1)<br>NMR(δ) CDCl$_3$<br>6.40∼7.00(m,3H), 5.70(m,2H),<br>5.30(b.t,1H), 4.50(b.s,3H),<br>4.00∼4.30(m,5H)<br>IR cm$^{-1}$ (neat) 3400, 2920, 1710 |
| 13 | α | COOH | 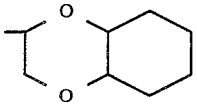 | oil | MS(m/e) 420(M$^+$)<br>NMR(δ) CDCl$_3$<br>5.50(m,2H), 5.10(b.s+t,4H),<br>3.00∼4.40(m,7H)<br>IR cm$^{-1}$ (neat) 3370, 2920, 1710 |
| 14 | β | COOH | 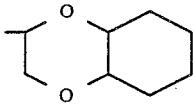 | oil | MS(m/e) 420(M$^+$)<br>NMR(δ) CDCl$_3$<br>5.60(m,2H), 5.30(b.t,1H),<br>4.75(b.s,3H), 3.50∼4.20(m,7H)<br>IR cm$^{-1}$ (neat) 3394, 2926, 1710 |
| 15 | α | COOH | 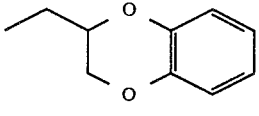 | oil | MS(m/e) 409(M$^+$ −19)<br>NMR(δ) CDCl$_3$<br>6.80(s,4H), 5.50(m,2H),<br>5.15(b.t,1H), 4.88(b.s,3H),<br>4.37(b.s,2H), 4.15(b.s,2H)<br>IR cm$^{-1}$ (neat) 3350, 2914, 1710 |
| 16 | β | COOH | 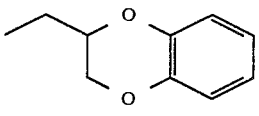 | oil | MS(m/e) 410(M$^+$ −H$_2$O)<br>NMR(δ) CDCl$_3$<br>6.80(s,4H), 5.65(m,2H),<br>5.20(b.t,1H), 4.40(b.s,3H),<br>3.95(m,3H), 3.65(m,1H)<br>IR cm$^{-1}$ (neat) 3350, 2914, 1710 |
| 17 | α | COOH | 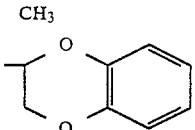 | oil | MS(m/e) 413(M$^+$ −15)<br>NMR(δ) CDCl$_3$<br>6.76(s,4H), 6.25∼5.75(b.s,3H),<br>5.15(b.t,1H), 4.40∼3.25(m,4H)<br>1.26(s,3H)<br>IR cm$^{-1}$ (neat) 3370, 2920, 1707 |
| 18 | β | COOH | 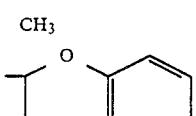 | oil | MS(m/e) 413(M$^+$ −15)<br>NMR(δ) CDCl$_3$<br>6.80(s,4H), 5.81∼5.43(m,2H),<br>5.43∼4.83(b.s+b.t,4H),<br>4.51∼3.52(m,4H), 1.22(s,3H)<br>IR cm$^{-1}$ (neat) 3394, 2920, 1707 |
| 19 | α | COOH | 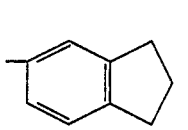 | oil | MS(m/e) 378(M$^+$ −H$_2$O)<br>NMR(δ) CDCl$_3$<br>7.20, 7.29(s+d.d,3H), 6.18, 6.27,<br>6.45, 6.70(d.d,2H), 5.20(b.t,1H),<br>3.80∼5.00(m,5H), 2.81(t,4H)<br>IR cm$^{-1}$ (neat) 3400, 2950, 1695 |
| 20 | β | COOH | 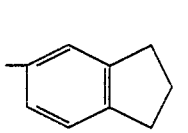 | oil | MS(m/e) 396(M$^+$)<br>NMR(δ) CDCl$_3$<br>7.15, 7.25(s+d,3H), 6.28, 6.36,<br>6.40, 6.75(d.d,2H),<br>4.60∼5.50(m,4H), 4.20∼4.60(m,1H),<br>4.20∼3.81(m,1H), 2.81(t,4H)<br>IR cm$^{-1}$ (neat) 3400, 2944, 1704 |

| Comp. | 15-Position | Z | B | appearance | Physical properties |
|---|---|---|---|---|---|
| 21 | α | COOH | (1-methyl-indanyl) | oil | MS(m/e) 378(M$^+$−36)<br>NMR(δ) CDCl$_3$<br>7.19(s,4H), 5.57(m,2H),<br>5.20(b.t,1H), 4.87(b.s,3H),<br>4.10∼4.48(m,1H), 3.21∼4.80(m,2H),<br>2.90(t,2H)<br>IR cm$^{-1}$ (neat) 3364, 2926, 1707 |
| 22 | β | COOH | (1-methyl-indanyl) | oil | MS(m/e) 378(M$^+$−36)<br>NMR(δ) CDCl$_3$<br>7.22(s,4H), 5.50(m,2H),<br>5.33(b.s+b.t,4H), 3.98∼4.50(m,1H),<br>3.10∼4.00(m,2H), 2.90(t,2H)<br>IR cm$^{-1}$ (neat) 3370, 2920, 1707 |
| 23 | α | COOH | (2-indanyl-5-NO$_2$) | oil | MS(m/e) 424(M$^+$−35)<br>NMR(δ) CDCl$_3$<br>7.80∼8.10(m,2H), 7.10∼7.40(m,1H),<br>5.75(b.s,3H), 5.45(m,2H),<br>5.18(b.t,1H), 3.80∼4.21(m,1H),<br>3.50∼3.80(m,1H), 2.88, 3.00(d,5H)<br>IR cm$^{-1}$ (neat) 3480, 2930, 1704 |
| 24 | β | COOH | (2-indanyl-5-NO$_2$) | oil | MS(m/e) 424(M$^+$−35)<br>NMR(δ) CDCl$_3$<br>7.85∼8.10(m,2H), 7.14∼7.40(m,1H),<br>5.60(m,2H), 5.25(b.s+b.c,4H),<br>4.00∼4.38(m,1H), 3.42∼3.96(m,1H),<br>2.89, 3.00(d+m,5H)<br>IR cm$^{-1}$ (neat) 3400, 2926, 1707 |
| 25 | α | COOH | (2-indanyl-5-OMe) | oil | MS(m/e) 409(M$^+$+1-H$_2$O), 407(M$^+$−1-H$_2$O)<br>NMR(δ) CDCl$_3$<br>6.45∼7.15(m,3H), 6.48(b.s,3H),<br>5.30∼5.60(m,2H), 5.16(b.t,1H),<br>3.40∼4.13(m,2H), 3.70(s,3H),<br>2.55∼3.20(d+m,5H)<br>IR cm$^{-1}$ (neat) 3334, 2920, 1707 |
| 26 | β | COOH | (2-indanyl-5-OMe) | oil | MS(m/e) 408(M$^+$−H$_2$O)<br>NMR(δ) CDCl$_3$<br>6.50∼7.31(m,3H), 5.45∼5.71(m,2H),<br>5.00∼5.43(b.s,3H), 5.21(b.t,1H),<br>3.44∼4.25(m,2H), 3.71(s,3H),<br>2.60∼3.21(m+d,5H)<br>IR cm$^{-1}$ (neat) 3376, 2926, 1707 |
| 27 | α | COOH | (2-indanyl-5-Cl) | oil | MS(m/e) 412(M$^+$−H$_2$O)<br>NMR(δ) CDCl$_3$<br>7.11∼7.03(d,3H), 5.98(b.s,3H),<br>5.37∼5.71(m,2H), 5.20(b.t,1H),<br>3.83∼4.20(m,1H), 3.38∼3.82(m,1H),<br>2.60∼3.20(m,5H)<br>IR cm$^{-1}$ (neat) 3370, 2926, 1707 |
| 28 | β | COOH | (2-indanyl-5-Cl) | oil | MS(m/e) 412(M$^+$−H$_2$O)<br>NMR(δ) CDCl$_3$<br>7.10∼7.04(d,3H), 5.80(b.s,3H),<br>5.31∼5.65(m,2H), 5.16(b.t,1H),<br>3.80∼4.16(m,1H), 3.38∼3.80(m,1H),<br>2.60∼3.20(m,5H)<br>IR cm$^{-1}$ (neat) 3382, 2926, 1704 |
| 29 | α | COOH | (benzo[1,3]dioxol-5-yl) | oil | MS(m/e) 381(M$^+$−1-H$_2$O)<br>NMR(δ) CDCl$_3$<br>6.85, 6.70,(S+d,3H),<br>6.61, 6.37, 6.22, 6.13(d.d,2H),<br>5.91(s,2H), 5.39∼4.70(b.t+b.s,4H),<br>4.70∼3.90(m,2H)<br>IR cm$^{-1}$ (neat) 3400, 2926, 1728 |
| 30 | β | COOH | (benzo[1,3]dioxol-5-yl) | oil | MS(m/e) 381(M$^+$−1-H$_2$O)<br>NMR(δ) CDCl$_3$<br>6.94, 6.80(s+d,3H), 5.85(s,2H),<br>6.56, 6.30, 6.90, 5.95(d.d,2H),<br>5.80∼5.70(b.t+b.s,4H),<br>4.60∼3.85(m,2H)<br>IR cm$^{-1}$ (neat) 3410, 2926, 1707 |

| Comp. | 15-Position | Z | B | appearance | Physical properties |
|---|---|---|---|---|---|
| 31 | α | COOH | 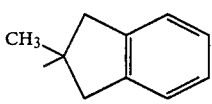 | oil | MS(m/e) 391(M$^+$—1-H$_2$O)<br>NMR(δ) CDCl$_3$<br>7.10(s.4H), 5.58(m.2H),<br>5.10(b.s+b.t.4H), 3.98~4.18(m.1H)<br>3.40~3.85(m.1H), 3.20, 2.950(d.2H)<br>2.78, 2.62(d.2H)<br>IR cm$^{-1}$ (neat) 3376, 2920, 1707 |
| 32 | β | COOH | 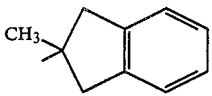 | oil | MS(m/e) 391(M$^+$—1-H$_2$O)<br>NMR(δ) CDCl$_3$<br>7.90(s.4H), 5.82(b.s,3H), 5.50(m.2H)<br>5.15(b.t,1H), 3.81~4.10(m.1H),<br>3.30~3.80(m.1H), 3.20, 2.96(d.2H)<br>2.71, 2.60(d.2H)<br>IR cm$^{-1}$ (neat) 3400, 2926, 1707 |

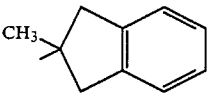

| Comp. | 15-Position | Z | B | appearance | Physical properties |
|---|---|---|---|---|---|
| 33 | α | COOH | 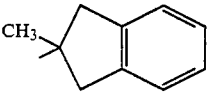 | White crystal<br>mp 59.0~60.3° C. | NMR(δ) CDCl$_3$<br>7.06(s,4H), 5.20~5.80(b.s+m+b.t,6H)<br>4.00(s,2H), 3.40~4.20(m,2H),<br>2.56, 2.70, 2.94, 3.13(d.d,4H),<br>1.50~2.54(m,9H), 1.10(s,3H)<br>IR cm$^{-1}$ (neat) 3400, 2920, 1728 |
| 34 | β | COOH | 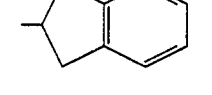 | White crystal<br>mp 52.1~53.2° C. | NMR(δ) CDCl$_3$<br>7.07(s,4H), 5.27~5.65(b.t+m,3H),<br>3.97(b.s,5H), 3.50~4.30(m,2H),<br>2.66, 2.70, 2.90, 3.10(d.d,4H),<br>1.47~2.55(m,9H), 1.11(s,3H)<br>IR cm$^{-1}$ (neat) 3406, 2920, 1728 |
| 35 | α | COOH | 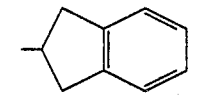 | White crystal<br>mp 106.0~107.0° C. | NMR(δ) CDCl$_3$<br>7.10(s,4H), 5.30~5.65(m+b.t,3H),<br>4.21(b.s,3H), 4.03(s,2H),<br>3.50~4.15(d+m,4H), 2.56~3.23(m,4H)<br>1.60~2.55(m,10H)<br>IR cm$^{-1}$ (neat) 3400, 2944, 1728 |
| 36 | β | COOH | 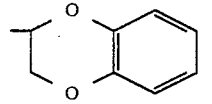 | White crystal<br>mp 105.0~106.0° C. | NMR(δ) CDCl$_3$<br>7.10(s,4H), 5.20~5.60(m+b.t,3H)<br>5.05(b.s,3H), 3.89~4.28(d+s,4H),<br>3.50~4.28(m,2H), 2.55~3.28(m,4H),<br>1.50~2.53(m,10H)<br>IR cm$^{-1}$ (neat) 3400, 2926, 1728 |
| 37 | α | COOH | 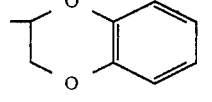 | White crystal<br>mp 106.1~106.9° C. | NMR(δ) CDCl$_3$<br>6.80(s,4H), 5.57~5.78(m,2H),<br>5.44(b.t,1H), 4.68(b.s,3H), 4.04(s,2H)<br>3.50~4.45(m,7H), 1.70~2.78(m,9H)<br>IR cm$^{-1}$ (neat) 3400, 2926, 1728 |
| 38 | β | COOH | 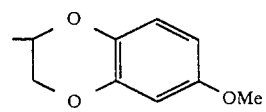 | White crystal<br>mp 66.3~67.3° C. | NMR(δ) CDCl$_3$<br>6.80(s,4H), 5.55~5.75(m,2H),<br>5.43(b.t,1H), 4.71(b.s,3H), 4.05(s,2H)<br>3.50~4.40(m,7H), 1.60~2.63(m,9H)<br>IR cm$^{-1}$ (neat) 3424, 2926, 1728 |
| 39 | α | COOH | | White crystal<br>mp 52.3~53.0° C. | NMR(δ) CDCl$_3$<br>6.28~6.89(m,3H), 5.51~5.71(m,2H),<br>5.43(b.t,1H), 5.20(b.s,3H), 3.70(s,3H)<br>3.54~4.50(m,9H), 1.60~2.60(m,9H)<br>IR cm$^{-1}$ (neat) 3400, 2920, 1728 |

-continued

| Comp. | 15-Position | Z | B | appearance | Physical properties |
|---|---|---|---|---|---|
| 40 | β | COOH | ![structure with dioxole and OMe] | White crystal mp 81.0~82.0° C. | NMR(δ) CDCl₃ 6.25~6.87(m,3H), 5.57~5.78(m,2H) 5.45(b.t,1H), 4.83(b.s,3H), 3.56~4.48(m,9H), 3.70(s,3H), 3.70(s,3H), 1.60~2.66(m,9H) IR cm⁻¹ (neat) 3424, 2920, 1728 |

[EXAMPLE 5~10]

[Process 1]

The starting compound(XI) is prepared from compound(VIII) as follow.

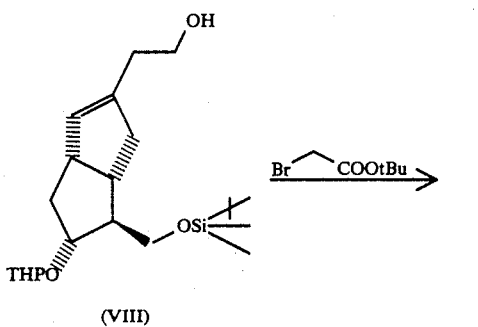

(VIII)

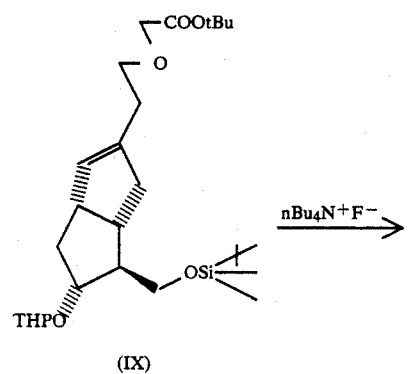

(IX)

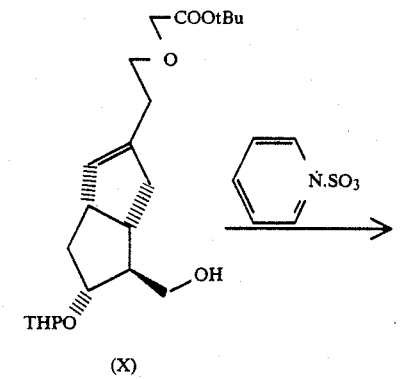

(X)

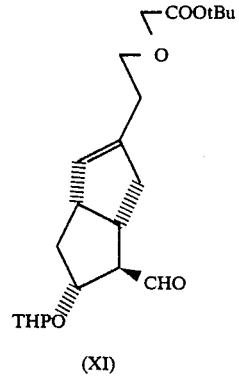

(XI)

To a mixture of 0.800 g (2.20 m mol) of homoallyl alcohol (compound VIII) and 6.3 ml (39.7 mmol) of tert-butyl bromoacetate in 18 ml dichlormethane was added, 1.8 ml of 50% NaOH solution and 46 mg of tetrabutyl ammonium bisulfate.

After stirring for 24 hr at room temp., water and ethan were added.

Ether solution was washed (brine), dried (Na₂SO₄) and evaporated in vacuo. The residue was chlomatographied on silica gel (Ether:n-hexan (1:10)). 0.634 g (61.3%) of compound(IX) was obtained.

N.M.R. (δ, CDCl₃) 5.31(b.s. 1H), 0.92(s. 9H), 0.65(s. 6H) 0.415 g of compound (IX) was dissolved in THF (4 ml) and 1.1 ml (1.06 mml) of tetra-butyl ammonium fluoride was added at 0° C. After stirring for 3 hr at 0° C., the reaction mixture was allowed to stand for 12 hr. After dilution with brine, the solution was extracted with ether and washed (brine), dried (Na₂SO₄) and evaporated. The residue was purified on silica gel (Ether:n-hexan (1:1)). 0.248 g of compound(X) was obtained. N.M.R. (δ, CDCl₃) 5.35(b.s. 1H), 5.69(m. H), 3.94(s. 2H), 1.47(s. 9H) To a solution of 0.05 g (0.126 mmol) of compound(X) in DMSO (1.4 ml) were added 0.05 ml of triethylamine and sulfur trioxide Pyridine complex (61 mg) in DMSO (1.4 ml) at room temp. After stirring for 30 min at same temp., water and ether were added. Ether extract was washed (H₂O), dried (Na₂SO₄) and evaporated. Compound(XI) (50 mg) was obtained.

The following compound 41~compound 46 were obtained in the same manner as the methods of Example 1~2.

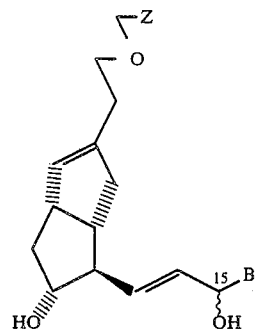

| Comp. | 15-Position | Z | B | appearance | Physical properties |
|---|---|---|---|---|---|
| 41 | α | COOH | 2-methylindanyl | White crystal mp 116.0~117.0° C. | NMR(δ) CDCl₃ 7.12(s,4H), 5.40~5.67(m,2H), 5.31(b.s,1H), 4.79(b.s,3H), 4.03(s,2H), 4.53, 4.61, 4.68(t,2H), 3.30~4.17(m,2H), 2.59, 2.72, 2.95, 3.12(d.d,4H), 2.78~3.18(m,1H), 1.71~2.49(m,9H), 1.11(s,3H) IR cm⁻¹ (neat) 3400, 2914, 1713 |
| 42 | β | COOH | 2-methylindanyl | White crystal mp 118.0~118.9° C. | NMR(δ) CDCl₃ 7.07(s,4H), 5.00~5.88(m+b.s,6H), 4.01(s,2H), 3.30~4.18(t+m,5H), 2.59, 2.70, 2.96, 3.12(d.d,2H), 3.20~3.78(m,1H), 1.50~2.47(m,9H), 1.00(s,3H) IR cm⁻¹ (neat) 3406, 2914, 1728 |
| 43 | α | COOH | indanyl | oil | NMR(δ) CDCl₃ 7.08(s,4H), 5.40~5.63(m,2H), 5.32(b.s,1H), 4.80(b.s,3H), 4.03(s,2H), 3.53, 3.60, 3.07(t,2H), 3.36~4.16(m,2H), 2.45~3.17(m,5H), 1.68~2.44(m,9H) IR cm⁻¹ (neat) 3400, 2914, 1728 |
| 44 | β | COOH | indanyl | oil | NMR(δ) CDCl₃ 7.08(s,4H), 5.11~5.60(m+b.s,6H), 4.02(s,2H), 3.54, 3.61, 3.68(t,2H), 3.40~4.11(m,2H), 2.50~3.27(m,5H), 1.69~2.49(m,9H) IR cm⁻¹ (neat) 3400, 2914, 1728 |
| 45 | α | COOH | benzodioxanyl | White crystal mp 61.5~63.0° C. | NMR(δ) CDCl₃ 6.80(s,4H), 5.56~5.78(m,2H), 5.35(b.s,1H), 4.82(b.s,3H), 4.04(s,2H), 3.54, 3.61, 3.68(t,2H), 3.40~4.43(m,5H), 2.08~3.16(m,1H), 1.80~2.64(m,9H) IR cm⁻¹ (neat) 3400, 2914, 1728 |
| 46 | β | COOH | benzodioxanyl | White crystal mp 53.5~54.2° C. | NMR(δ) CDCl₃ 6.80(s,4H), 5.56~5.77(m,2H), 5.35(b.s,1H), 5.20(b.s,3H), 4.06(s,2H), 3.56, 3.63, 3.70(t,2H), 3.37~4.47(m,5H), 2.80~3.16(m,1H), 1.77~2.64(m,9H) IR cm⁻¹ (neat) 3400, 2920, 1728 |

What is claimed is:
1. A compound of formula:

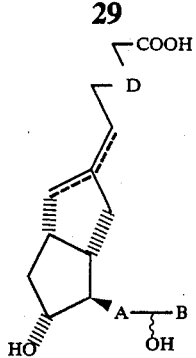

Wherein:

A is —CH=CH— or —C≡C— group; B is substituted or unsubstituted indanyl group, substituted or unsubstituted benzodioxanyl group, substituted or unsubstituted benzodioxolanyl group or 2,3,5,6,7,8-hexahydrobenzodioxanyl group, D is —CH$_2$— or —O— atom; ~OH is α or β-configuration of OH group,

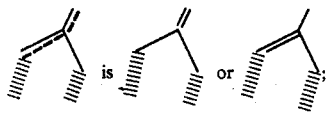

or pharmaceutically acceptable alkali addition salts thereof.

2. A compound according to claim 1 wherein D is —O— and

3. A compound according to claim 1 wherein D is —O— and

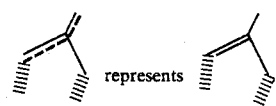

4. A compound according to claim 1 wherein A is —CH=CH— and B is an indanyl, benzodioxanyl or benzodioxolanyl group, which are optionally substituted by a lower alkyl, lower alkyloxy, halogen or 2,3,5,6,7,8-hexahydrobenzodioxanyl group.

5. A compound according to claim 1 wherein A is a —C≡C— group.

6. A compound according to claim 1 wherein A is a —CH=CH— group and B represents an indanyl group which is optionally substituted by a lower alkyl, lower alkyloxy, halogen or nitro group.

7. A compound according to claim 1 wherein A is a —CH=CH— group and B represents a benzodioxanyl group which is optionally substituted by a lower alkyl, lower alkyloxy, halogen or nitro group.

8. A compound according to claim 1 wherein A is a —CH=CH— group and B represents a benzodioxanyl group which is optionally substituted by a lower alkyl, lower alkyloxy, halogen or nitro group.

9. A compound according to claim 1 to 8 wherein ~OH has α-configuration.

10. A compound according to claim 1 to 8 wherein ~OH has β-configuration.

11. An anti-ulcerative composition cpmrising an amount, effective to inhibit gastric ulcer, of a compound defined in claim 1 in combination with a pharmaceutically acceptable carrier.

12. An anti-thrombotic composition comprising an amount, affective to inhibit thrombosis, of a compound defined in claim 1 in combination with a pharmaceutically acceptable carrier.

13. An anti-hypertensive composiotion comprising an amount, effective to inhibit hypertension, of a compound defined in claim 1 in combination with a pharmaceutically acceptable carrier.

14. A method of preparing a compound of the formula:

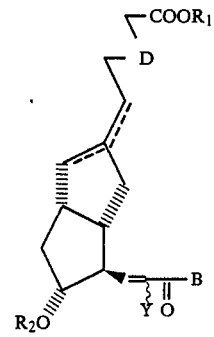

wherein R$_1$ is a lower alkyl, R$_2$ is a protecting group of hydroxy group. Y is hydrogen or halogen atom, B is substituted or unsubstituted indanyl group, substituted or unsubstituted benzodioxanyl group, substituted or unsubstituted benzodioxolanyl group or 2,3,5,6,7,8-hexahydrobenzodioxanyl group; D is —CH$_2$— or —O—

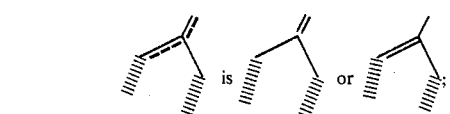

which is comprises:

reacting a compound of formula:

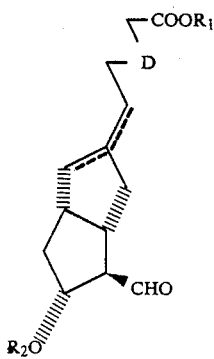

Wherein R$_1$, R$_2$, D and

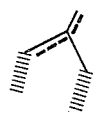
are defined above,
With a compound of formula:
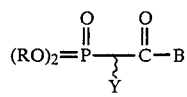
wherein R is a lower alkyl group of $C_{1\sim3}$, Y and B are as defined above.
* * * * *